(12) United States Patent
Mayoras, Jr.

(10) Patent No.: US 10,827,985 B2
(45) Date of Patent: *Nov. 10, 2020

(54) NOTIFICATION SYSTEM OF DEVIATION FROM PREDEFINED CONDITIONS

(71) Applicant: Stryker Corporation, Kalamazoo, MI (US)

(72) Inventor: Richard C. Mayoras, Jr., Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/578,589

(22) Filed: Sep. 23, 2019

(65) Prior Publication Data
US 2020/0015762 A1   Jan. 16, 2020

Related U.S. Application Data

(63) Continuation of application No. 15/783,246, filed on Oct. 13, 2017, now Pat. No. 10,420,517, which is a (Continued)

(51) Int. Cl.
*G08B 5/22* (2006.01)
*A61B 5/00* (2006.01)
(Continued)

(52) U.S. Cl.
CPC ............ *A61B 5/746* (2013.01); *A61B 5/002* (2013.01); *A61B 5/0022* (2013.01); *A61B 5/1117* (2013.01); *A61B 5/6892* (2013.01); *A61B 5/7275* (2013.01); *A61B 5/7282* (2013.01); *A61B 5/742* (2013.01); *G08B 21/043* (2013.01); *G08B 21/0453* (2013.01);
(Continued)

(58) Field of Classification Search
CPC ....... A61B 5/746; A61B 5/002; A61B 5/0022; A61B 5/6892; A61B 5/7275; A61B 5/7282; A61B 5/742; G61H 50/20; G08B 21/043; G08B 21/0453; G08B 21/0461
See application file for complete search history.

(56) References Cited

U.S. PATENT DOCUMENTS

| | | | |
|---|---|---|---|
| 7,746,218 B2 * | 6/2010 | Collins, Jr. | ............... G07C 3/00 340/286.07 |
| 7,852,208 B2 | 12/2010 | Collins, Jr. et al. | |

(Continued)

FOREIGN PATENT DOCUMENTS

| EP | 2289394 A1 | 3/2011 |
|---|---|---|
| EP | 2392304 A1 | 12/2011 |

OTHER PUBLICATIONS

Extended European Search Report and Annex, dated Nov. 13, 2014, for the European patent application 13176111.6. corresponding to U.S. Appl. No. 13/836,259.

*Primary Examiner* — Phung Nguyen
(74) *Attorney, Agent, or Firm* — Warner Norcross + Judd LLP

(57) ABSTRACT

The present invention includes a healthcare system for capturing and maintaining patient healthcare records and employing information in the records to proactively alert hospital workers to a condition that places patient health at risk.

20 Claims, 9 Drawing Sheets

Related U.S. Application Data continuation of application No. 14/873,704, filed on Oct. 2, 2015, now Pat. No. 9,788,800, which is a continuation of application No. 13/836,259, filed on Mar. 15, 2013, now Pat. No. 9,149,190.

(60) Provisional application No. 61/672,740, filed on Jul. 17, 2012.

(51) Int. Cl.
| | | |
|---|---|---|
| *G08B 21/04* | (2006.01) | |
| *G16H 50/20* | (2018.01) | |
| *A61B 5/11* | (2006.01) | |
| *G06F 19/00* | (2018.01) | |
| *G16H 40/20* | (2018.01) | |
| *G16H 40/67* | (2018.01) | |

(52) U.S. Cl.
CPC ......... *G08B 21/0461* (2013.01); *G16H 50/20* (2018.01); *G06F 19/3418* (2013.01); *G16H 40/20* (2018.01); *G16H 40/67* (2018.01)

(56) References Cited

U.S. PATENT DOCUMENTS

| | | |
|---|---|---|
| 8,284,047 B2 | 10/2012 | Collins, Jr. et al. |
| 8,593,284 B2 * | 11/2013 | Tallent .................. A61B 5/1117 340/573.1 |
| 8,604,917 B2 | 12/2013 | Collins et al. |
| 8,655,680 B2 | 2/2014 | Bechtel et al. |
| 8,736,453 B2 | 5/2014 | Wilson et al. |
| 2002/0151990 A1 * | 10/2002 | Ulrich ................. G06F 19/3418 700/65 |
| 2007/0010719 A1 * | 1/2007 | Huster ................. A61B 5/0022 600/300 |
| 2008/0281638 A1 | 11/2008 | Weatherly et al. |
| 2011/0074571 A1 | 3/2011 | Collins, Jr. et al. |
| 2014/0022079 A1 | 1/2014 | Wilson et al. |

\* cited by examiner

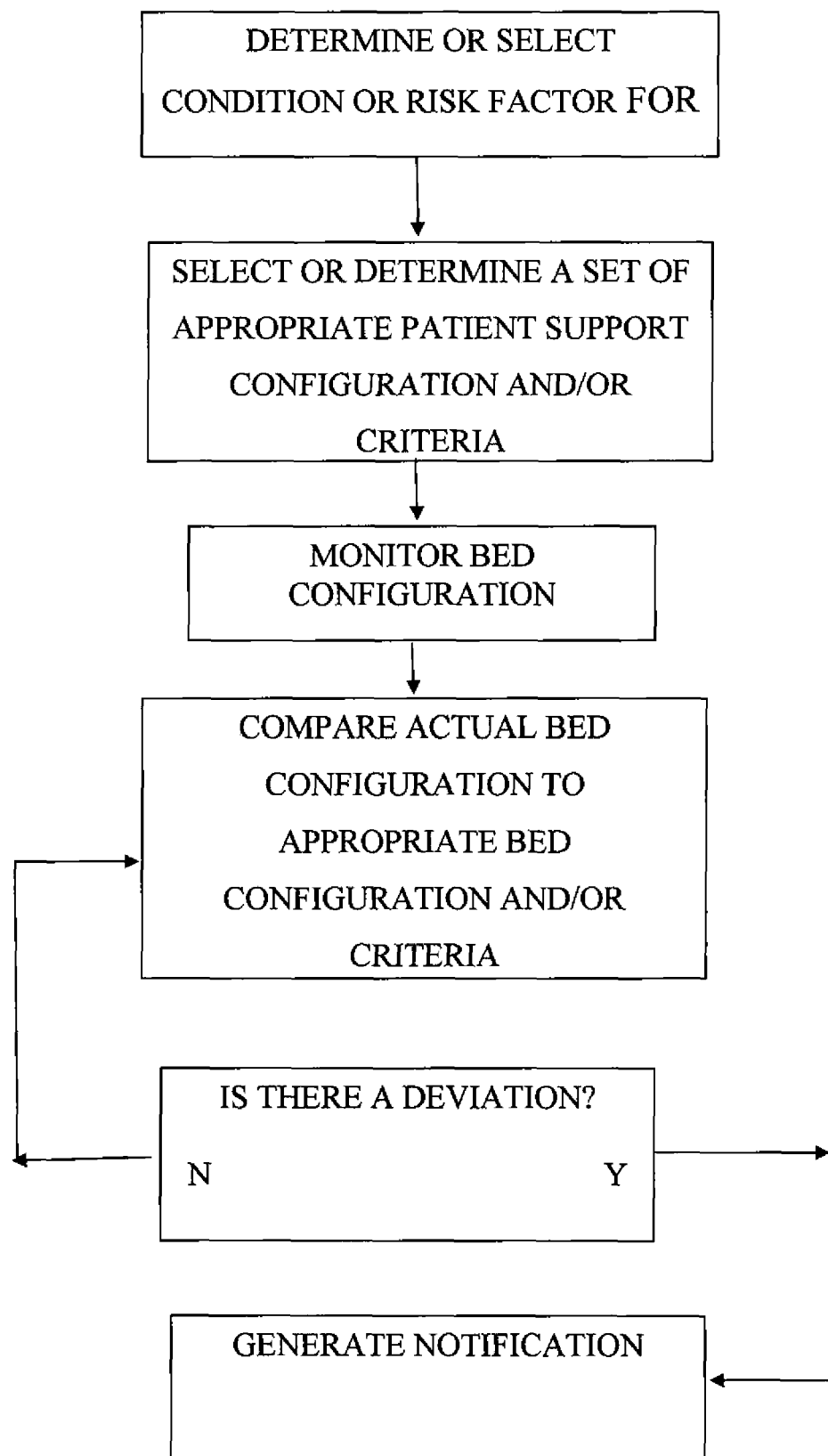

FIG. 3A

MINIMUM BED CONFIG. / FALL RISK TYPE

| RISK TYPE | MINIMUM BED CONFIGURATION |
|---|---|
| HIGH | THREE RAILS UP, BED LOW, BRAKE ON |
| MEDIUM | TWO RAILS UP, BRAKE ON |
| LOW | BRAKE ON |

FIG. 3B

PATIENT FALL RISK PROFILE

| PATIENT ID | FALL RISK TYPE |
|---|---|
| PATIENT 1 | HI |
| PATIENT 2 | MED |
| PATIENT n | LO |

FIG. 3C

PATIENT FALL RISK PROFILE

| PATIENT ID | FALL RISK CRITERIA | BED CONFIGURATION |
| --- | --- | --- |
| PATIENT 1 | CAN'T STAND UNASSISTED | ALL RAILS UP BED MED. HEIGHT |
| PATIENT 2 | NEED ASSISTENCE TO WALK | THREE RAILS UP |
| PATIENT n | CAN'T WALK | ALL RAILS UP, BED LOW HEIGHT |

FIG. 3D

CURRENT BED CONFIGURATION STATE

PATIENT ID/FALL RISK
BED ID
STATUS OF ALL BED PROPERTIES

EVENT NOTIFICATION MODULE

NOTIFICATION SYSTEM OF DEVIATION FROM PREDEFINED CONDITIONS

This is a continuation of U.S. patent application Ser. No. 15/783,246, filed Oct. 13, 2017, entitled NOTIFICATION SYSTEM OF DEVIATION FROM PREDEFINED CONDITIONS, now U.S. Pat. No. 10,420,517, which is a continuation of U.S. patent application Ser. No. 14/873,704, filed Oct. 2, 2015, entitled NOTIFICATION SYSTEM OF DEVIATION FROM PREDEFINED CONDITIONS, now U.S. Pat. No. 9,788,800, which is a continuation of U.S. patent application Ser. No. 13/836,259, filed Mar. 15, 2013, entitled NOTIFICATION SYSTEM OF DEVIATION FROM PREDEFINED CONDITIONS, now U.S. Pat. No. 9,149,190, which claims the benefit of U.S. patent application Ser. No. 61/672,740, filed Jul. 17, 2012, entitled NOTIFICATION OF PATIENT RISK CONDITIONS, which are hereby incorporated by reference herein in their entireties.

TECHNICAL FIELD AND BACKGROUND OF THE INVENTION

The present disclosure relates generally to healthcare systems for capturing and maintaining patient healthcare records and employing information in the records to proactively alert hospital workers to a condition that places patient health at risk.

A healthcare provider, such as a hospital, typically admits and treats some number of patients on a daily basis. Upon admission to the hospital, a healthcare worker can create a record that includes medical and/or personal information associated with each patient. Depending upon the size of the hospital, the healthcare provider can create and maintain a very large number of these medical records, and such records are typically created and then stored as an electronic medical record (EMR) in a healthcare system. Depending upon the size of the hospital, the healthcare system can operate in a single computational device, such as a personal computer or other device, or the healthcare system can be distributed in a plurality of computational devices that are connected to over a network (healthcare system network or simply the Network) to one or more servers which operate to, among other things, capture and store the electronic medical records. In addition to including patient medical information, an EMR can also include the identity and location (hospital room) of a hospital bed to which a patient is assigned. Hospital beds are available that include physical and physiological sensors which are connected over the Network to the Healthcare System. Information collected by the sensors can be processed at the bed by a controller or can be transmitted to the Hospital System for processing and storage in an EMR associated with the patient currently occupying the bed.

While physiological measures of a patient's health can be employed to proactively alert healthcare workers of an impending patient health crisis, healthcare systems do not currently operate to proactively alert healthcare workers to a condition at the bed, such as a hospital bed configuration, which may be unsatisfactory for a given patient based on the patient's condition or risk.

SUMMARY OF THE INVENTION

The present invention includes a notification system that takes into account the condition or risk factor of a given patient. The benefits to a patient in a healthcare system that can operate to proactively warn healthcare workers of an adverse patient condition are apparent. The ability to identify which patients may suffer possible, future adverse health events, such as a stroke or congestive heart failure, can either extend or save a patient's life.

In one form of the invention, a notification system includes a patient support and a patient support monitoring system that is configured to detect and monitor when the patient support's configuration is unsuitable for a given patient based on the patient's condition or risk factor(s) and then generate a notification of an unsatisfactory configuration at the patient support.

In one aspect, the patient's condition or risk factor is determined or selected, for example, by a staff member and then is designated for that patient Based on the designated condition or risk factor for the patient, the patient support monitoring system may automatically select or determine a set of appropriate patient support configurations and/or criteria, such as side rails up or down, bed exit alarmed, head of bed angle, patient movement, as default configurations and/or criteria for that patient. Alternately or in addition, the system can have the set of appropriate patient support configurations and/or criteria entered, for example, by a caregiver either to override the default or establish the default configurations and/or criteria.

In another aspect, the patient support monitoring system may include a network interface and one or more sensors in communication with the network interface for detecting the actual configuration and/or criteria of the patient support. The network interface is in communication with, for example, a hospital network or nurse call station, which receives the status or signal(s) of the sensor(s) from the network and compares the status or signal(s) to the appropriate patient support configuration and/or criteria to determine if the actual patient support configuration and/or criteria deviate from the appropriate patient support configuration and/or criteria.

In yet a further aspect, when the patient support monitoring system determines that actual patient support configuration and/or criteria of the patient support deviate from the appropriate patient support configuration and/or criteria, the patient support monitoring system will generate the notification of an unsatisfactory configuration at the patient support.

For example, the notification may include alerts to staff, for example, including mobile alerts, pop-up displays, for example at the nurse call station, generate alarms, for example at the patient support, documentation for storage, for example, for reports or for archival, anecdotal, training, or six sigma purposes.

In another aspect, the notification level may be selected. For example, the caregiver or the system itself may select and designate a high priority notification level, for example, for a high risk factor patient, a medium priority notification level, for example, for a moderate risk factor patient, and a low priority notification level, for example, for a low risk factor patient. For example, a high risk factor might be a high risk fall factor.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

BRIEF DESCRIPTION OF THE DRAWINGS

The present invention can be best understood by reading the specification with reference to the following Figures, in which:

FIG. 2A is a schematic of a notification of the present invention;

FIG. 3A is a table of exemplary configurations for a given predefined condition;

FIG. 3B is a table of a format of a listing of patients and their associated risk type;

FIG. 3C is a table of a patient risk profile showing exemplary information, e.g. risk criteria and configuration, for a given patient;

FIG. 3D is a table of information included in a current bed configuration state;

DETAILED DESCRIPTION OF PREFERRED EMBODIMENTS

Figure 1:
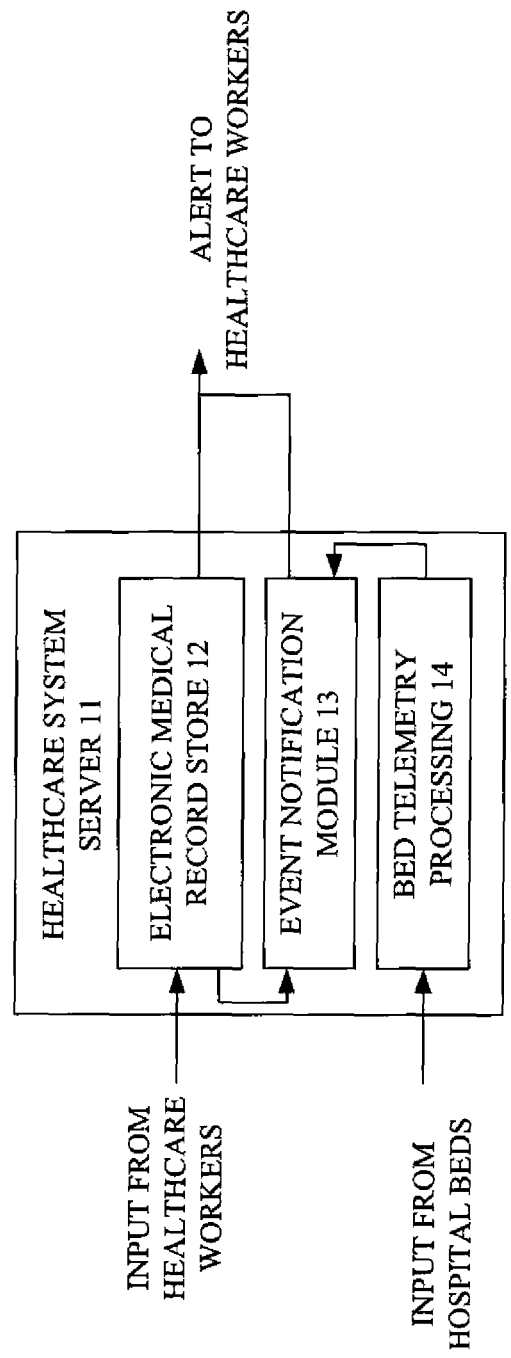
FIG. 1 is a diagram of a Hospital Healthcare System.

Referring to FIG. 1, the numeral 10 designates a hospital healthcare system 10, which is configured to allow it to receive and store information from both healthcare workers and hospital beds. A server 11 is shown connected over one or more links to the healthcare system 10 network. The server 11 generally operates to capture and maintain a store 12 of patient EMRs, and it has a bed telemetry processing function 14 that operates to capture and process information received from hospital beds connected to the network. The sever 11 also has an event notification module 13 that can access information in the EMR store 12 and bed telemetry information to determine whether an alert message should be sent to a hospital worker or call point connected to the healthcare system 10. Alternatively, a database management system (DBMS) running on the healthcare system server 11 can operate to maintain the patient electronic medical records and maintain hospital bed configuration status information in a database 15 where the information can be accessed by the event notification module 13.

Healthcare organizations, such as a hospital or other care facility, have identified many patient health risks that are directly associated with care the patient receives while a resident in the facility. Some of these risks are associated with the physiological health of the patient, such as the risk of stroke or heart attack, or the risk of congestive heart failure for instance. Other types of risk can be associated with the physical well being of a patient, such as whether a patient is a fall risk. Typically upon admission to a healthcare organization, each patient can be evaluated to determine the condition of the patient and/or risk factor for the patient, for example, the degree to which they are at risk of falling or developing pressure ulcers. This evaluation process can include a physical examination, for example, to observe a patient's motor skills and balance, and/or it can include simply observing a patient or questioning the patient about their healthy history, for example, whether they have had surgery, are diabetic or have poor circulation for other reasons. Regardless of the protocol employed to quantify the condition or risk, such as a fall risk of a particular patient, a condition or risk can be assigned to each patient and entered into a healthcare system, such as the healthcare system 10 described earlier, and stored in the patients EMR. A patients EMR can be easily accessed by a healthcare worker, such as a nurse, nurses aid or physician, in order to determine whether or not a patient has a condition or risk, such as a risk of falling, and if so the level or degree to which the patient is at risk. Depending upon the patient's risk level, the patient's bed can be set up or configured by the healthcare worker in a manner that can prevent the patient from, for example, developing pressure sores or accidentally falling out of the bed, or at the bed can be set up so that the patient can more easily enter and exit the bed.

Figure 2:
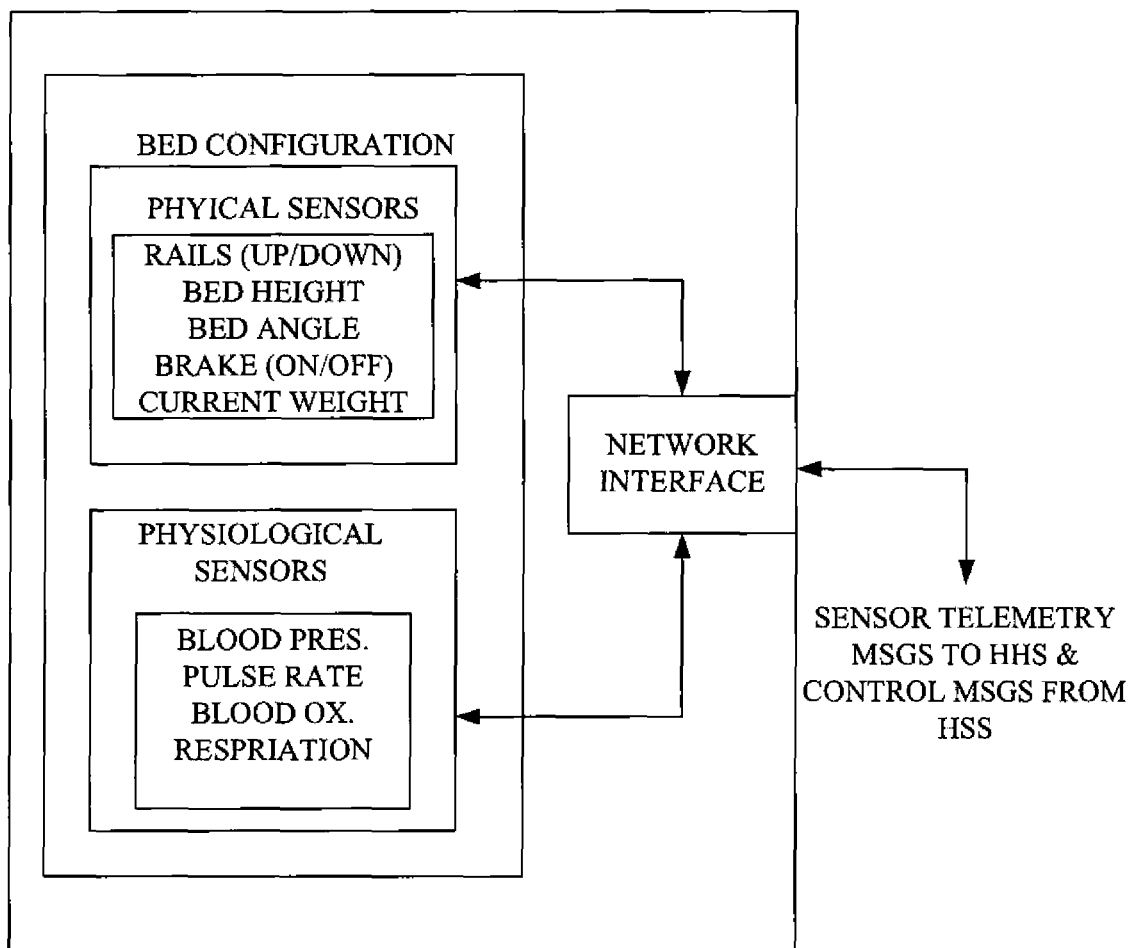
FIG. 2 is a diagram of an intelligent hospital bed.

Referring to FIG. 2, a hospital bed may be configured to include a number of different types of sensors, and the bed can be connected, over the network, to a healthcare system. Some bed sensors function to detect a patients weight in one or more positions on the surface of a bed or movement of the patient on the bed, while other bed sensors may detect whether or not bed side rails are engaged in a full up position or not. Some bed sensors operate to detect the angle at which one portion of a bed meets another portion of the bed, and still other bed sensors can detect physiological characteristics of a patient such as heart rate, respiratory rate, blood pressure to name only three characteristics. The sensors included in each bed can be connected to a central bed control mechanism which can operate to receive/capture information from each of the sensors, and can process the information prior to transmission over a network link to a healthcare system or send the sensor information to the healthcare system for processing. The healthcare system can then process the information received from the bed sensors to determine whether a healthcare worker should be notified of an event, such as a patient having exited their bed or a change in a patient's physiological measurement such as heart rate, blood pressure or respiratory rate as detected by bed sensors. Typically, a healthcare system can generate an alert in the event that a change to any one or more of a patient's physiological measurements is greater than a threshold amount, and the healthcare system is typically not capable of determining whether the physiological changes to the patient place the patient at risk of some adverse health event, such as a stroke.

Referring to FIGS. 2 and 2A, a notification system of the present invention may include one or more patient supports and a patient support monitoring system. In the illustrated embodiment, the patient support comprises a hospital bed, but it should be understood that the notification system of the present invention may include other types of patient supports, including stretchers, cots etc. However, for ease of description, reference hereinafter will be made to a hospital bed. As will be more fully described below, the present invention includes a notification system that takes into account the condition or risk factor of a given patient.

Referring to FIG. 2A, the patient support monitoring system is configured to detect and monitor when the patient support's configuration is unsuitable for a given patient based on the patient's condition or risk factor(s) and then generate a notification of an unsatisfactory configuration at the patient support. For example, predefined conditions for a given patient risk and/or condition profile, for example, may include different medical conditions (e.g. diabetes, surgery etc.) or clinical conditions of the patient that render the patient more susceptible to injury (e.g. pressure ulcers), as well as other risk factors include fall risk factors, described more fully below. In addition, the patient support monitoring system maybe configured to detect and monitor when the patient support's configuration is suitable for a given patient based on the patient's condition or risk factor(s) and then generate a notification of a satisfactory configuration at the patient support.

The patient's condition or risk factor is determined or selected, for example, by a staff member and then is designated for that patient. Based on the designated condition or risk factor for the patient, the patient support monitoring system may automatically select or determine a set of appropriate patient support configurations and/or criteria, such as side rails up or down, bed exit alarmed, head of bed angle, patient movement, as default configurations and/or criteria for that patient. Alternately or in addition, the system can have the set of appropriate patient support configurations and/or criteria entered, for example, by a caregiver either to override the default or establish the default configurations and/or criteria.

For example, the patient support may include a network interface and one or more sensors in communication with the network interface for detecting the actual configuration and/or criteria of the patient support by way of the sensors. The network interface is in communication with, for example, a hospital network or nurse call station, which receives the status or signal(s) of the sensor(s) from the network and compares the status or signal(s) to the appropriate patient support configuration and/or criteria to determine if the actual patient support configuration and/or criteria deviate from the appropriate patient support configuration and/or criteria. For a detailed description of a suitable communication system using a bed to transmit such information, reference is made to co-pending application Ser. No. 13/570,934, filed on Aug. 9, 2012, entitled PATIENT SUPPORT APPARATUS WITH IN-ROOM DEVICE COMMUNICATION, which is incorporated by reference herein in its entirety and commonly owned by Stryker Corporation of Kalamazoo, Mich.

When the patient support monitoring system determines that actual patient support configuration and/or criteria of the patient support deviate from the appropriate patient support configuration and/or criteria, the patient support monitoring system will generate the notification of an unsatisfactory configuration at the patient support. For example, the notification may include alerts to staff, for example, including mobile alerts, pop-up displays, for example at the nurse call station, generate alarms, for example at the patient support, or may generate documentation for storage, for example, for reports or for archival, anecdotal, training, or six sigma purposes.

Optionally, the notification level may be selected. For example, the caregiver or the system itself may select and designate a high priority notification level, for example, for a high risk factor patient, a medium priority notification level, for example, for a moderate risk factor patient, and a low priority notification level, for example, for a low risk factor patient. For example, a high risk factor might be a high risk fall factor.

For example, when a patient has an elevated patient fall risk, the hospital bed configuration may lead to a patient accidentally falling out of their hospital bed, or falling while attempting to enter their bed. The formats of and information comprising an illustrative fall risk type, a patient fall risk profile and a current bed configuration are now described with reference to FIG. 3A-3D respectively. FIG. 3A identifies three generic fall risk types (high, medium, low), with each fall risk type corresponding to a particular minimum hospital bed configuration. In this case, the minimum bed configuration specified for a high fall risk type patient requires that three bed rails in the full up position, the bed height is adjusted to be low and a bed brake is on. These fall risk types can be defined and entered into a healthcare system by a healthcare organization based upon a corpus of patient fall risk information included in EMR's over some period of time.

FIG. 3B is illustrative of one or more patient risk profiles, such as fall risk profiles. All of the profiles can be stored in a patient EMR. A plurality of patients, patient 1 to patient n (with n being an integer value), are identified, and each of the patients identified is assigned a generic risk type. For example, patient 1 is assigned risk type high, and so forth to patient n which is assigned a low risk type. Alternatively, a patient's risk profile may not include a generic fall risk type, but instead may be comprised of one or more risk criteria. For example, a fall risk criteria can be identified during an initial patient fall risk assessment and can include a description of a patient's symptoms (physical and/or physiological) that can affect the patient's mobility or ambulatory characteristics. Such a fall risk criteria description can include a description of assistance a patient needs in order to stand up, sit down and/or walk. The criteria description can indicate that a patient cannot stand without being assisted by a hospital worker, or that they can stand without assistance but they are not able to walk without the assistance of a cane/walker/hospital worker. The criteria description can indicate that due to blood pressure issues the patient becomes light headed when they attempt to stand or that the patient suffers from vertigo. In the event that a patients fall risk profile does not include a generic fall risk type, but rather includes one or more fall risk criteria, then a patient fall risk profile may be formatted according to FIG. 3C.

FIG. 3C shows a plurality of patient fall risk profiles each of which include three fields. A first field includes patient identification information, a second field includes fall risk criteria information and a third field includes bed configuration information specifically tailored to each patients fall risk criteria. With respect to patient 1, the fall risk criteria field includes information indicating that the patient is not able to stand without assistance from a hospital worker, and the corresponding bed configuration profile is then specified to include how the bed should be configured to prevent the patient from accidentally falling out of the bed and bed configuration information that allows the patient to easily enter and exit their bed, which in this case is that all bed rails should be in the full up position and the bed should be set to a medium height above the floor.

FIG. 3D is an example format of a current bed configuration record that is comprised of at least the identity of a patients bed, the identify of a patient assigned to the bed and their fall risk assessment, and which includes the current status of the bed properties (current bed status) as determined by the healthcare system 10 from information/telemetry received from the bed sensors. Bed properties in the context of this description refers to, among other things, the number and types of bed rails included on a hospital bed, whether the bed has a height sensor, whether a bed can tilt, whether the bed includes weight sensors and the position of the weight sensors in the bed. In the preferred embodiment, the current bad property status can be, among other things, a determination that one or more rails are fully up or down, a determination as to the height of the bed above floor level and the tilt angle of the bed.

Figure 4:
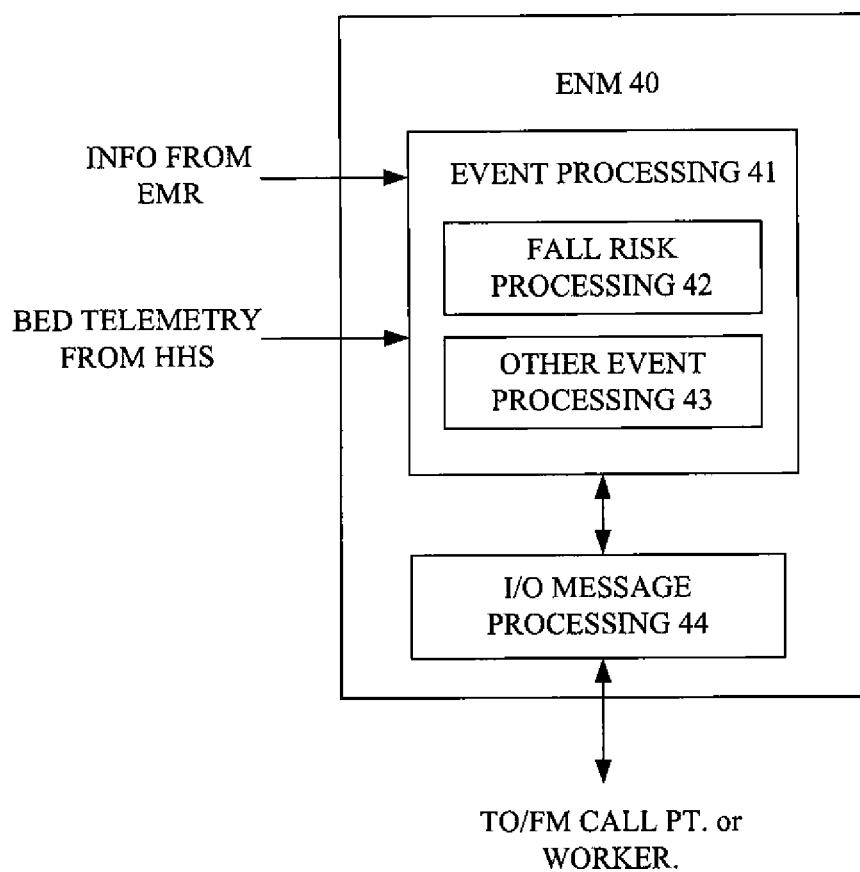
FIG. 4 is a functional block diagram of one embodiment of an event notification module.

FIG. 4 is illustrative of an event notification module (ENM) 40 that can be implemented in a server connected to a healthcare network, such as the healthcare network described with reference to FIG. 1. The ENM 40 operates on information comprising a patient EMR, information relating to a current bed status and a generic fall risk type to determine whether to generate and send an alarm to a hospital worker or call station indicating that a patient fall risk is greater than a selected threshold. The threshold can be set to a particular numerical value or it can be a minimum bed configuration similar to the minimum bed configuration described with reference to FIG. 3A. Alternatively, the ENM 40 does not employ the generic fall risk type to determine whether to generate an alert, but rather uses patient fall risk criteria. The ENM 40 is generally comprised of an event processing function 41, an input/output message (alarm) processing function 44 and may or may not have access to a database, such as the database 15 described earlier with reference to FIG. 1. The event processing function 41 can be comprised of a fall risk processing function or client 42 and other event processing clients as necessary for processing different classes of events. The fall risk processing client 42 can operate on, among other things, information in a patient's EMR and current bed configuration information to determine whether to send an alert to a call point or healthcare worker. In the event that an alert is generated by the event processing function 41, the information in the alert is sent to the input/output message processing function 44 which operates to determine which of one or more healthcare workers or call points should receive the alert. After receiving the alert, the healthcare worker can correct/modify the current bed configuration to at least meet the minimum hospital bed properties configuration necessary to mitigate the patient fall risk. Further, the healthcare system can detect that the bed configuration is modified/corrected by the healthcare worker to meet the minimum bed properties configuration and either cancel the earlier transmitted alert or send another alert indicating that the patient is no longer at risk of falling.

Figure 5:
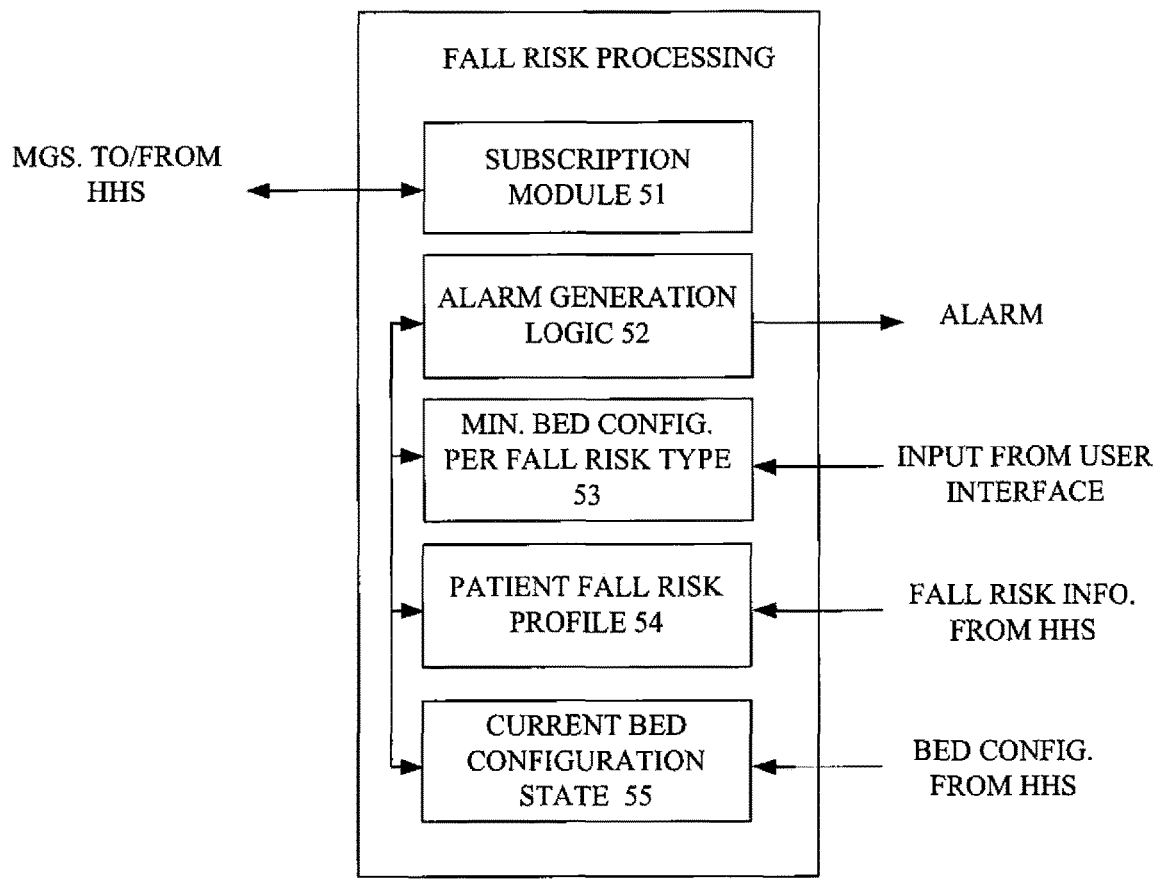
FIG. 5 is a functional block diagram of one embodiment of a fall risk processing client.

The fall risk processing function or client 42 is now described in greater detail with reference to FIG. 5. The client 42 is comprised of a subscription module 51, alarm generation logic 52, a store of or access to a store of minimum bed configuration information 53 per patient fall risk type, a store or access to a store of patient fall risk profile information 54, and a store or access to a store of current bed configuration state or information 55. Although the stores 53, 54 and 55 are illustrated in FIG. 5 as being local to the client 42, this does not have to be the case. These stores can be located in temporary storage (buffer memory) associated with the client 42 or these stores can be located in a main memory in the server, or it can be located in any memory that is accessible by the client 42 over a local or wide area network. The store(s) described herein can be implemented in any one or a combination of computer data storage technologies, such as semiconductor, magnetic or optical technologies for example. The subscription module 51 generally operates to send standard subscription request messages to one or more servers, connected to a healthcare system network, that can store information of interest to the client, such as EMR or bed configuration information. Once a response to a subscription request is received by the module 51, the event processing function 41 will automatically start to receive information currently stored in the record associated with the subscription request. This information can be for example, information regarding the current configuration state of one or more beds and this state information can be saved in a store 55 associated with or accessible by the client 42. Alternatively, the client 42 may not subscribe to receive bed configuration state information, but rather a healthcare server can periodically publish current bed configuration state information to some or all of the healthcare clients connected to the healthcare network.

Continuing to refer to FIG. 5, the minimum bed configuration store 53 is comprised of information similar to that described with reference to FIG. 3A, the patient fall risk profile store 54 is comprised of information similar to that described with reference to either FIG. 3B or 3C, and the current bed configuration state store 55 is comprised of information similar to that described with reference to FIG. 3D. Finally, the alarm generation logic 52 is comprised of a computer program that operates to determine whether or not to generate an alarm based upon information included in the stores 53, 54 and 55 (or alternative only stores 54 and 55). More specifically, in one embodiment the logic 52 can operate to examine a patient's fall risk profile, associated minimum bed configuration, and the current bed configuration state. If the current bed configuration state indicates that the patient is in their bed, the logic proceeds to determine if the current bed configuration meets the minimum bed configuration for the patient (i.e., which rails are up or down, bed heights, etc.). If the current bed configuration meets the minimum bed configuration for that patient, then the logic 52 does not generate an alert. On the other hand, if the current bed configuration does not meet the minimum bed configuration for that patient, then an alert is generated. Alternatively, the logic 52 only needs to examine the patient fall risk profile 54 if the fall risk criteria and the bed configuration profile information are stored here.

The operation of the alarm generation logic 52 will now be described with reference to the flow diagram of FIG. 6. While FIG. 6 and the following description are directed to an embodiment in which fall risk criteria and patient bed configuration information corresponding to the patients fall risk criteria are not entering into the healthcare system server, it should be understood that this information can be entered into the system and employed by the logic 52 in order to determine whether or not to generate an alert. In step 1 of the flow diagram, a hospital worker can define one or more generic patient fall risk types and enter these types into a healthcare system of storage on a server such as server 11 in FIG. 1. These fall risk types can be identified by the terms high (high fall risk), medium (medium fall risk), low (low fall risk), they can be identified in descending numerical order from a highest to lowest fall risk, or the fall risk type can be define in some other manner. Each generic fall risk type can be associated with a set of generic patient fall risk criteria. The fall risk criteria set can include, among other things, the degree to which a patient can balance while standing and the type of assistance (cane, walker, hospital worker) the patient needs in order to remain standing, it can include whether the patient has any broken limbs, and it can include physiological measures such as whether the patient has vertigo. Each fall risk type can be associated with a minimum bed configuration which is comprised of such things as whether one or more bed rails are up or down, the tilt angle of the bed and the height of the bed above the floor level. In step 2, a hospital worker can evaluate whether or not a patient is at risk or falling, and if they are the process proceeds to Step 4, otherwise the process ends at step 3. In Step 4, the hospital worker can evaluate the degree to which the patient is at risk of falling and assign them to one of the fall risk types entered into the system in Step 1. The assigned risk type can then be entered into the patients EMR. At this point, a healthcare system has information that is necessary in order to generate an alert indicating that a patient may be at risk of falling at some point in the future.

Figure 6A:
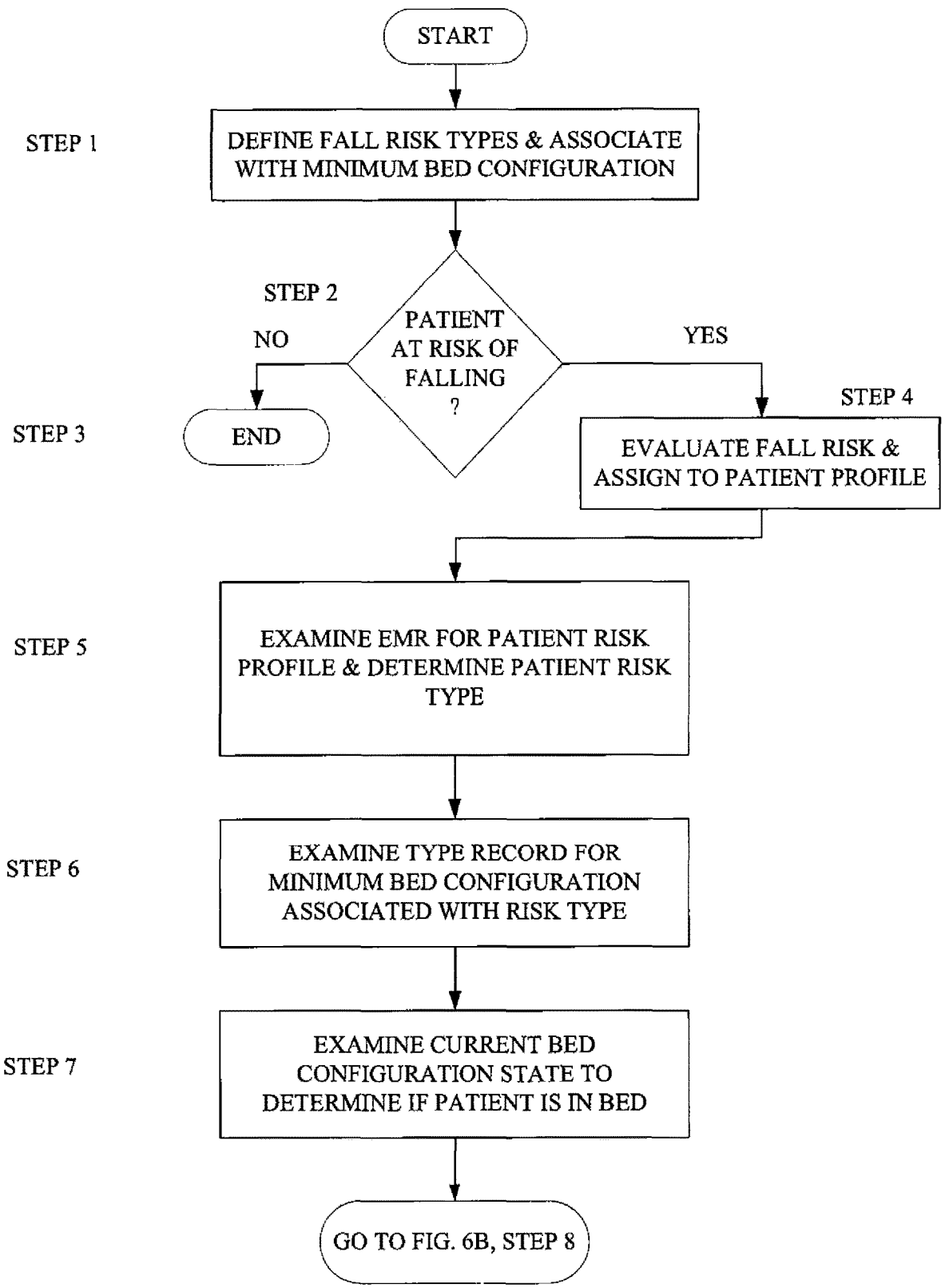
FIGS. 6A and 6B illustrate a logical flow diagram of one embodiment of the invention.
Figure 6B:
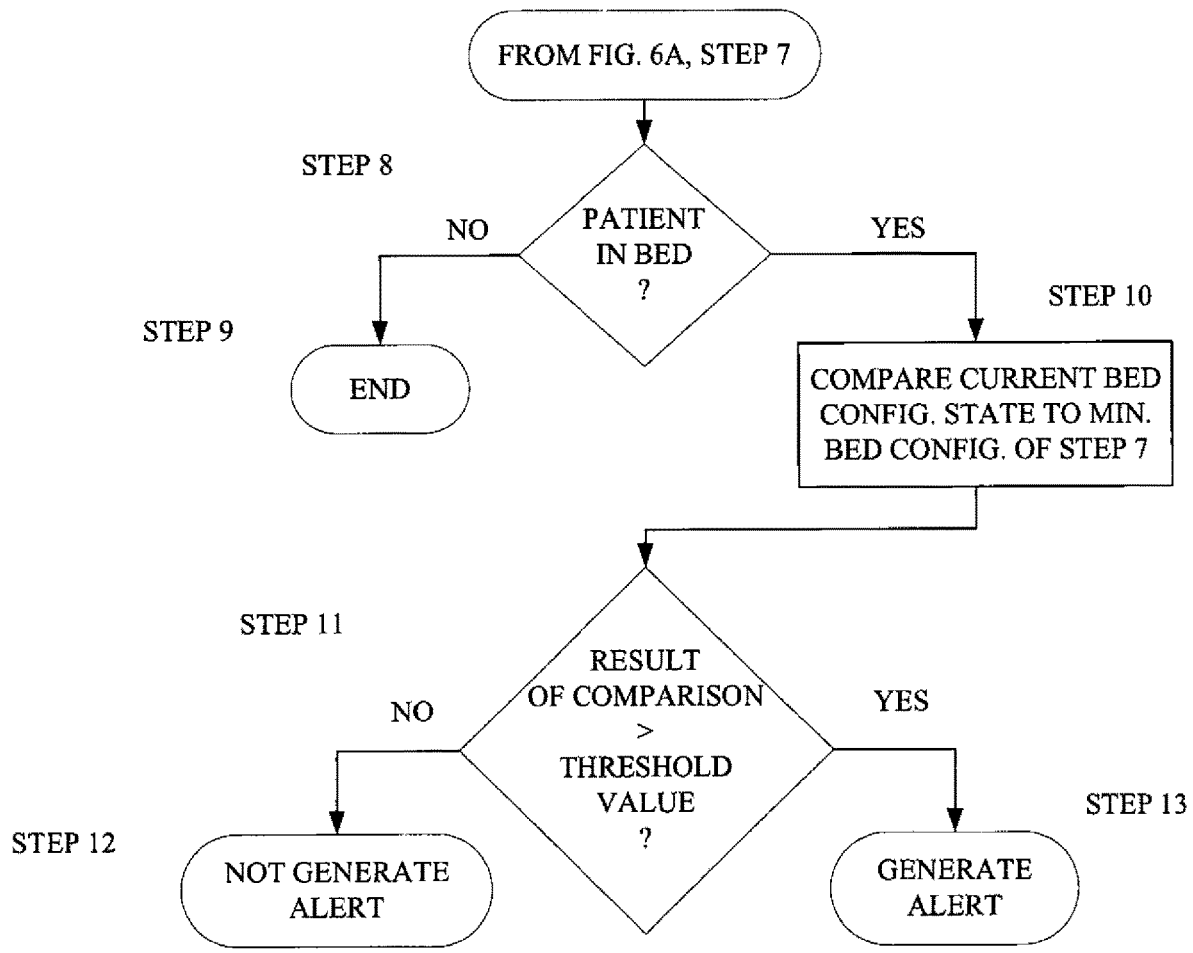

Continuing to refer to FIG. 6, in Step 5 of the process the logic 52 can examine a patient's fall risk profile stored in the patient's EMR in order to determine the patients fall risk type. Based upon the fall risk type, the logic 52 can then, in Step 6, look up minimum bed configuration information stored in the table/record described with reference to FIG. 3A. Next, in Step 7 the logic 52 can then examine the current bed configuration state described with reference to FIG. 3D, and compare this current state to the minimum bed configuration information detected as the result of Step 6. Then, in Step 8 the logic 52 can employ information detected in Step 7 to determine whether a patient is currently in their bed, and if not the process proceeds to Step 9 and no alert is generated. On the other hand, if in Step 8 the logic 52 determines that a patient is in their bed, the process proceeds to Step 10 where the state of the current bed configuration detected in Step 7 is compare to the minimum bed configuration for that patient detected in Step 6. If, in Step 11, the comparison performed in Step 10 determines that the current bed configuration does not meet the minimum bed configuration necessary to adequately protect the patient from falling out of the bed (i.e. the value of the comparison is greater than a pre-determined threshold value), the process proceeds to Step 13 and an alert is generated and sent to a call station or directly to a hospital worker. On the other hand, the process proceeds to Step 12 if the result of the comparison performed in Step 10 indicates that the current bed configuration does meet the minimum configuration necessary to prevent the patient from fall out of the bed.

Software for remotely setting up parameters to be monitored at the bed and monitoring the parameters, which could be for example a thin client or fat client application, reference is made to patent application Ser. No. 61/790,823, filed on even date herewith, entitled PATIENT SUPPORT APPARATUS WITH REMOTE COMMUNICATIONS.

Accordingly, the present invention provides a healthcare system that proactively alerts healthcare workers to a bed configuration change that elevates a patient's risk, for example, of falling out of their bed, or falling while attempting to enter their bed. With the knowledge that a patient is currently in their bed or not in their bed, knowing the patient's condition or risk profile, knowing the minimum hospital bed configuration associated with the patients risk profile, and knowing the current bed configuration state, the healthcare system can generate a notification, such as an alert to one or more healthcare workers, indicating that the patient's risk of injury is elevated above an acceptable level. More specifically, the present invention can provide a healthcare system that can include a patient risk processing function that operates to compare a current patient bed configuration to a minimum bed configuration corresponding to a patient's condition or risk profile, and if the current bed configuration does not meet the minimum bed configuration (less than the minimum configuration), then an alert can be generated by the healthcare system for transmission to one or more healthcare workers. After receiving the alert, the healthcare worker can modify the current bed configuration to meet the minimum bed configuration and the healthcare system can either clear the previously transmitted alert and/or it can send another alert indicating that the bed configuration has been corrected. With the knowledge that the current configuration of a patient's hospital bed places them in an elevated risk of injury, accidental patient injuries can be mitigated or prevented.

Therefore, it will be understood that the embodiments shown in the drawings and described above are merely for illustrative purposes, and are not intended to limit the scope of the invention which is defined by the claims which follow as interpreted under the principles of patent law including the doctrine of equivalents.

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert but which can be used independently and/or combined with other features. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

I claim:
1. A notification system comprising:
a healthcare system;
a patient support having a configuration, a network interface in communication with the healthcare system, and a monitoring system having sensors detecting the configuration of the patient support, and the healthcare system receiving information from the monitoring system about the configuration of the patient support through the network interface;
a set of generic risks entered into the healthcare system, each generic risk having a risk type associated therewith;
an input to the healthcare system configured to allow a healthcare worker to select one generic risk of the generic risks and to assign the selected generic risk to a patient supported on the patient support, wherein the monitoring system automatically associates a minimum patient support configuration with the patient supported on the patient support based on the generic risk assigned to the patient; and the healthcare system generating a notification to a caregiver when the monitoring system detects when a sensed configuration of the patient support deviates from the minimum patient support configuration associated with the patient.

2. The notification system according to claim 1, wherein the healthcare system also includes room information of the patient support.

3. The notification system according to claim 1, wherein the healthcare system is configured to generate multiple notification levels when the healthcare system detects the sensed configuration deviates from the minimum patient support configuration associated with the generic risk assigned to the patient.

4. The notification system according to claim 1, wherein the healthcare system is configured to detect when a patient support configuration is modified or corrected to meet the minimum patient support configuration.

5. The notification system according to claim 4, wherein the healthcare system is configured either cancel the notification or send another notification indicating that the patient is no longer at risk.

6. The notification system according to claim 1, further comprising at least one physiological sensor to sense a physiological condition of the patient supported thereon, the monitoring system in communication with the at least one physiological sensor, and the monitoring system having a default setting for the physiological condition and operable to generate the notification when the sensor detects when a sensed physiological condition deviates from the default setting.

7. The notification system according to claim 6, wherein the physiological condition includes a condition selected from the group consisting of heart rate, blood pressure, and respiratory rate.

8. The notification system according to claim 1, further comprising at least one physiological sensor in communication with the monitoring system to sense a physiological condition of the patient supported on the patient support, the healthcare system receiving information from the monitoring system about the physiological condition of the patient through the network interface; and the healthcare system processing the information received from the physiological sensor to determine whether the healthcare worker should be notified of an event.

9. The notification system according to claim 8, wherein the healthcare system generates an alert in the event that a change to a patient's physiological condition as detected by the physiological sensor varies a threshold amount from a default setting for the physiological condition.

10. The notification system according to claim 1, wherein the healthcare system stores documentation regarding the sensed condition of the patient support.

11. A notification system comprising:
a healthcare system, the health care system having a network and a server in communication with the network, the server including a collection of data, the collection of data including patient risk profiles and minimum patient support configurations;
a patient support having a configuration, a network interface in communication with the healthcare system, and a monitoring system having sensors detecting the configuration of the patient support, and the healthcare system receiving information from the monitoring system about the detected configuration of the patient support through the network interface; and
the healthcare system configured to assign a patient risk profile to a patient supported on the patient support and to automatically associate a minimum patient support configuration for the patient based on the patient risk profile assigned to the patient, and the healthcare system configured to compare the current patient support configuration as detected by the monitoring system to the minimum patient support configuration associated with the patient supported on the patient support and to generate a notification to a caregiver when the detected configuration of the patient support deviates from the minimum patient support configuration associated with the patient.

12. The notification system according to claim 11, wherein the healthcare system also includes room information of the patient support.

13. The notification system according to claim 11, wherein the healthcare system is configured to generate multiple notification levels when the healthcare system detects the detected configuration deviates from the minimum patient support configuration associated with the patient.

14. The notification system according to claim 11, wherein the healthcare system is configured to detect when the detected configuration of the patient support is modified or corrected to meet the minimum patient support configuration.

15. The notification system according to claim 14, wherein the healthcare system is configured either cancel the notification or send another notification indicating that the patient is no longer at risk.

16. The notification system according to claim 11, further comprising at least one physiological sensor in communication with the monitoring system to sense a physiological condition of the patient supported on the patient support, the healthcare system receiving information from the monitoring system about the physiological condition of the patient through the network interface; and the healthcare system processing the information received from the physiological sensor to determine whether a healthcare worker should be notified of an event.

17. The notification system according to claim 16, wherein the healthcare system generates an alert in the event that a change to a patient's physiological condition as detected by the physiological sensor varies a threshold amount from a default setting for the physiological condition.

18. The notification system according to claim 16, wherein the physiological condition includes a condition selected from the group consisting of heart rate, blood pressure, and respiratory rate.

19. The notification system according to claim 16, wherein the healthcare system stores documentation regarding the sensed physiological condition of the patient.

20. The notification system according to claim 11, wherein the healthcare system stores documentation regarding the detected configuration of the patient support.

* * * * *